United States Patent [19]

Wilson et al.

[11] Patent Number: 4,988,508

[45] Date of Patent: Jan. 29, 1991

[54] USE OF BENZYL FORMATE, D-CARVONE AND D-PULEGONE AND MIXTURES OF SAME AS INSECT ATTTRACTANTS

[75] Inventors: Richard A. Wilson, Westfield, N.J.; Jerry F. Butler, Gainesville, Fla.; Donald Withycombe, Lincroft, N.J.; Braja D. Mookherjee, Holmdel, N.J.; Ira Katz, West Long Branch, N.J.; Kenneth R. Schrankel, Tinton Falls, N.J.

[73] Assignees: International Flavors & Fragrances Inc., New York, N.Y.; The University of Florida, Gainesville, Fla.

[21] Appl. No.: 2,016

[22] Filed: Jan. 9, 1987

[51] Int. Cl.⁵ ............................................. A01N 25/00
[52] U.S. Cl. .......................................... 424/84; 424/78
[58] Field of Search ................................... 424/84, 78

[56] References Cited

PUBLICATIONS

Beroza et al., "Materials Tested as Insect Attractants", Agricultural Handbook No. 239, Agricultural Research Service, USDA (1963).
Chemical Abstracts 98:125687j (1983).

Primary Examiner—Allen J. Robinson
Attorney, Agent, or Firm—Arthur L. Liberman

[57] ABSTRACT

Described are the uses of benzyl formate having the structure:

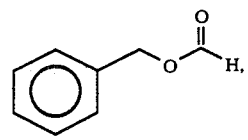

d-carvone having the structure:

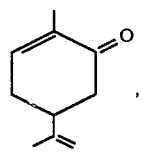

and d-pulegone having the structure:

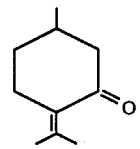

taken alone or taken in combination as attractants for house flies (*Musca domestica* L. (Diptera:Muscidae)). The benzyl formate, d-carvone and di-pulegone taken alone or in combination find utility primarily as bait enhancers for acute toxins and/or trapping devices.

8 Claims, 4 Drawing Sheets

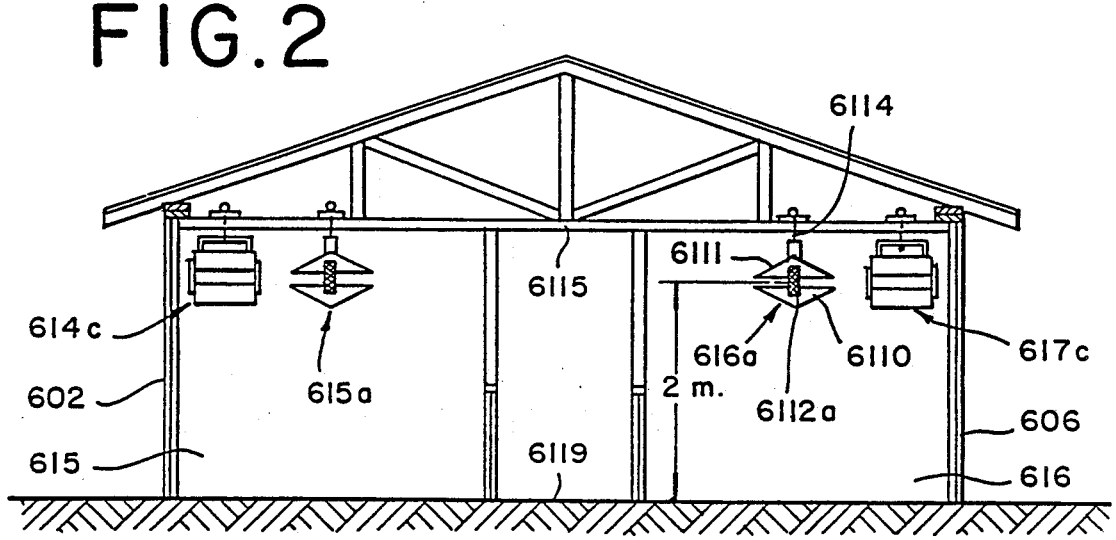
FIG.2
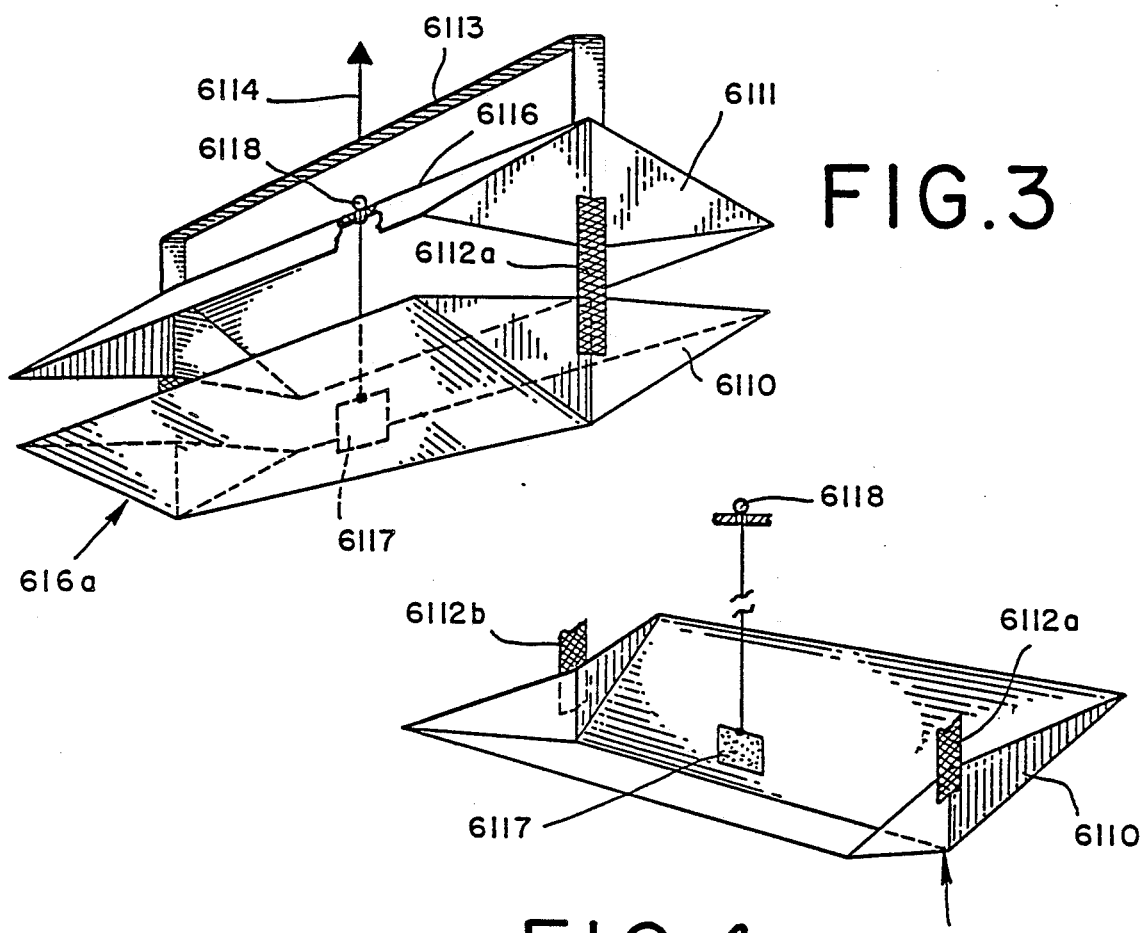
FIG.3
FIG.4

USE OF BENZYL FORMATE, D-CARVONE AND D-PULEGONE AND MIXTURES OF SAME AS INSECT ATTTRACTANTS

BACKGROUND OF THE INVENTION

This invention relates to insect attractants for house flies (*Musca domestica L.* (Diptera:Muscidae)). More particularly this invention relates to compositions of matter containing benzyl formate, d-carvone and d-pulegone or combination of benzyl formate, d-carvone and d-pulegone as attractants for *Musca domestica L.* (Diptera:Muscidae).

Fast intercontinental travel and trade are stepping up changes of importing nonindigenous insect pests into the United States. Attractants, or lures, can be of considerable aid in facilitating the early detection of such insect pests, and they are of vital importance in measuring the progress of a program aimed at eradicating a species that has become established.

In Agriculture Handbook No. 239 published by the Agricultural Research Service of the United States of America Department of Agriculture issued in June 1963 entitled, "Materials Tested As Insect Attractants", compiled by M. Beroza and N. Green, benzyl formate having the structure:

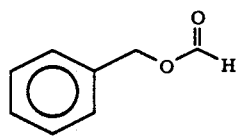

is indicated to have low attractancy indeces "1" on a scale of 1 to 3 for the Oriental Fruit Fly, the Melon Fly, the Mediterranean Fruit Fly and the Mexican Fruit Fly.

Methyl homologues and dimethyl analogues of benzyl formate are indicated in the Agricultural Handbook No. 239 to have in many cases attractances for the Oriental Fruit Fly, the Melon Fly, the Mediterranean Fruit Fly and the Mexican Fruit Fly as follows:

The compound having the structure:

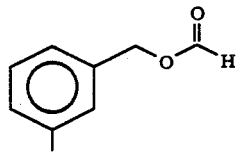

attracts the Oriental Fruit Fly and the Mexican Fruit Fly only slightly ("1" on a scale of 1 to 3) and to a greater extent the Mediterranean Fruit Fly ("2" on a scale of 1 to 3).

The compound having the structure:

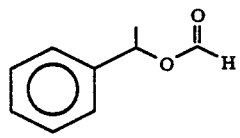

is only indicated to attract the Gypsy Moth only slightly ("1" on a scale of 1 to 3) and is indicated to show no attractancy for any other flies.

The compound having the structure:

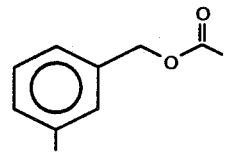

is also indicated to only attract the Gypsy Moth. However, the compound having the structure:

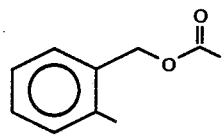

attracts the Oriental Fruit Fly only slightly ("1" on a scale of 1 to 3) and the Mexican Fruit Fly only slightly ("1" on a scale of 1 to 3) and the house fly only slightly ("1") on a scale of 1 to 3) but attracts the Mediterranean Fruit Fly intensely ("3" on a scale of 1 to 3).

The compound having the structure:

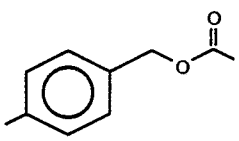

attracts the Oriental Fruit Fly to an extent of "2" on a scale of 1 to 3, the Melon Fly to the extent of "1" on a scale of 1 to 3, the Mediterranean Fruit Fly to the extent of "3" on a scale of 1 to 3, and the Mexican Fruit Fly to the extent of "1" on a scale of 1 to 3 but shows no attractancy for the house fly.

The compound having the structure:

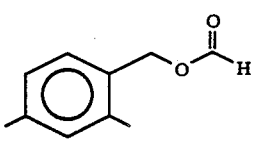

attracts the Oriental Fruit Fly at a level of "1" on a scale of 1 to 3, the Mediterranean Fruit Fly at a level of "2" on a scale of 1 to 3, and the Mexican Fruit Fly at a level of "1" on a scale of 1 to 3 but is not shown to attract the house fly.

The compound having the structure:

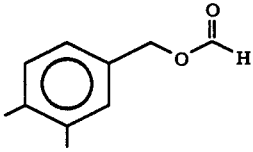

is shown to have an attractancy at the level of "1" on a scale of 1 to 3 for the Oriental Fruit Fly, the Mediterranean Fruit Fly, the Mexican Fruit Fly as well as the Gypsy Moth and the house fly.

Carvone (Item No. 2656) having the structure:

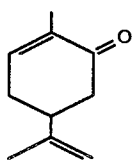

is indicated in Agriculture Handbook No. 239 to have an attractancy of "1" on a scale of 1 to 3 for the Oriental Fruit Fly, the Mexican Fruit Fly, and the Mediterranean Fruit Fly; but is not indicated to show any attractancy for the house fly.

Menthone having the structure:

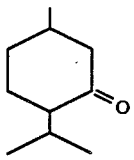

(Item No. 2688) is indicated in Agriculture Handbook No. 239 to have an attractancy for the Oriental Fruit Fly, the Melon Fly, the Mediterranean Fruit Fly and the Mexican Fruit Fly of "1" on a scale of 1 to 3 but is not shown to have any attractancy for the house fly.

Nothing in the prior art discloses the use of benzyl formate, d-carvone or d-pulegone taken alone or in combination in attracting certain species of insects including *Musca domestica L.* (Diptera:Muscidae) at a high level; higher than standard Commercial Products, e.g., GOLDEN MALRIN®.

BRIEF DESCRIPTION OF THE DRAWINGS

FIG. 2 is a cut-away side elevation view (schematic) indicating the positioning of sticky traps in a test barn taken along lines 2—2 of FIG. 1.

FIG. 3 is a perspective schematic view of a test sticky trap showing the positioning of the slow release material suspended inside of the trap structure.

FIG. 4 is a cut-away section in perspective of the sticky trap system of FIG. 3.

SUMMARY OF THE INVENTION

Figure 1:
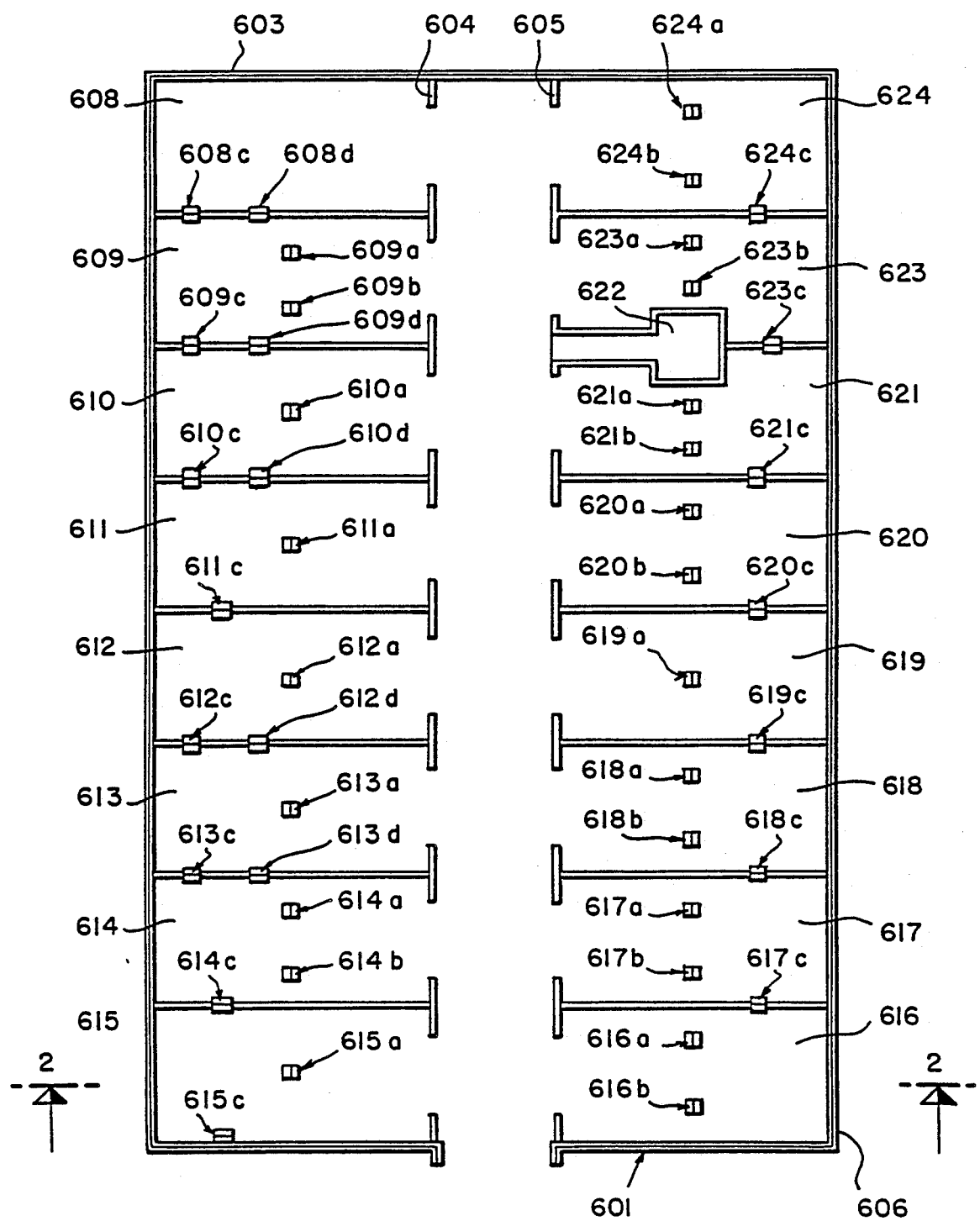
FIG. 1 is a schematic top view of the location of insect traps containing formulated slow release insect attractants and control materials (known attractant, GOLDEN MALRIN® fly baid).

Our invention relates to the use of benzyl formate, d-carvone, d-pulegone or combinations thereof, e.g., mixtures of benzyl formate, and d-carvone, mixtures of benzyl formate and d-Pulegone, mixtures of d-carvone and d-pulegone and mixtures of benzyl formate, d-carvone and d-pulegone as attractants for house flies (*Musca domestica L.* (Diptera:Muscidae)). A trapping system which is the basis of a first testing technique used in testing the efficacy of the benzyl formate, d-carvone, d-pulegone and combinations thereof is a standard ZOECON® sticky trap consisting of a ZOECON PHEROCON® 1C trap with a 2 cm×2 cm strip of formulated slow release attractant suspended on a paper clip inside the trap. The traps were placed in a goat barn and are suspended from the rafters. Trap placement was replicated in the four quadrants of the barn. Traps were placed in the barn for seven days and the insects collected were identified and counted. Evidence of insects visiting the traps were also counted as insect specks inside or outside to the traps. All test materials were compared with a standardized check treatment consisting of 0.5 grams of GOLDEN MALRIN® fly bait inside of the slow release packet hung like the other compounds.

Our invention also relates to the formation of insect attractant-containing polymeric pellets by means of introduction into a single screw or twin screw extruder of, in series, thermoplastic polymer followed by insect attractant which is compatible with the thermoplastic polymer, in turn, followed by introduction of a gaseous blowing agent or blowing agent which will produce a gas which is inert to the polymer and to the insect attractant, e.g., benzyl formate, d-carvone, d-pulegone or combinations thereof.

In the alternative, the use of the foaming agent can be omitted.

The nature of the extruder utilized in this aspect of our invention to form the polymeric insect attractant particles of our invention may be either single screw or double screw. Thus, the types of extruder that can be used are disclosed at pages 246–267 and 332–349 of the Modern Plastics Encyclopedia, 1982–1983 published by the McGraw-Hill Publishing Company, the disclosure of which is incorporated by reference herein. More specifically, examples of extruders which are useable in carrying out this aspect of our invention (with modification for introduction of insect attractant downstream from introduction of the polymer and optionally with a further modification that the gaseous blowing agent is introduced still further downstream from the point of introduction of insect attractant) are as follows:

1. The Welex "Super Twinch" 3.5" extruder manufactured by Welex Incorporated, 850 Jolly Road, Blue Bell, Pa. 19422;
2. Krauss-Maffei twin screw extruder manufactured by the Krauss-Maffei Corporation/Extruder Division, 3629 West 30th Street South, Wichita, Kan. 67277;
3. Modified Sterling Model 4000 and 5000 series extruder manufactured by Sterling Extruder Corporation of 901 Durham Avenue, South Plainfield, N.J.;
4. CRT ("Counter-Rotating Tangential") Twin Screw Extruder manufactured by Welding Engineers, Inc. of King of Prussia, Pa. 19406;
5. The Leistritz Twin Screw Dispersion Compounder manufactured by the American Leistritz Extruder Corporation of 198 U.S. Route 206 South, Somerville, N.J. 08876;
6. The ZSK Twin Screw Co-Rotating Extruder manufactured by the Werner & Pfleiderer Corporation of 663 East Crescent Avenue, Ramsey, N.J. 07446;
7. The Farrel Extruder manufactured by Farrel Connecticut Division, Emhart Machinery Group, Ansonia, Conn. 06401;
8. The MPC/V Baker Perkins Twin Screw Extruder manufactured by the Baker Perkins Inc. Chemical Machinery Division of Saginaw, Mich. 48601; and
9. The Berstorff Single Screw, Twin Screw, or Foam Extrusion Equipment manufactured by Berstorff Corporation, P. 0. Box 240357, 8200-A Arrowridge Boulevard, Charlotte, N.C. 28224.

In producing the insect attractant-containing polymer particles of our invention, various polymers may be utilized, for example, low density polyethylene, high density polyethylene, polypropylene, the co-polymer of ethylene and acetate, and polyvinyl chloride. More specifically, the polymers used in the practice of our invention may be co-polymers of ethylene and a polar vinyl monomer selected from (a) vinyl acetate; (b) ethyl acrylate; (c) methyl acrylate; (d) butyl acrylate and (e) acrylic acid including the hydrolyzed co-polymer of ethylene and vinyl acetate. Preferred co-polymers are ethylene vinyl acetate with about 9 to 60% vinyl acetate and ethylene/ethyl acrylate with about 6 to 18% ethyl acrylate.

Resins of the type disclosed for use as co-polymers are commercially available in the molding powder form. For example, ethylene vinyl acetate co-polymers are marketed the O.D E.I. duPont de Nemours Company under the tradename "ELVAX®" and by the Arco Polymer Division under the trademark "DYLAND®" and by the Exxon Corporation of Linden, New Jersey under the trademark "DEXXON®". Ethylene/ethyl acrylate co-polymers are marketed Union Carbide Corporation under the tradename "EEA RESINS®".

The polymer is added to the single screw or twin screw extruder at a feed rate in the range of from about 80 up to about 300 pounds per hour while maintaining the temperature in the screw extruder between about 160° and about 240° C. If the polymer or co-polymer powder is added to the extruder at a reference "barrel segment", then the insect attractant is added to the extruder under pressure downstream from the addition point of the polymer at 1 or more "barrel segments" S-2, S-3, S-4, S-5, S-6, S-7, S-8 or S-9.

Thus, the invention provides a process for forming insect attractant-containing polymeric particles such as polymeric pellets which include a relatively high concentration of insect attractants. The insect attractant added at "barrel segments" "S-2, S-3, S-4, S-5, S-6, S-7, S-8 or S-9 of the single screw or twin screw extruder is to be compatible with the polymer added at "barrel segment" S-1 of the single screw or twin screw extruder.

The proportion of insect attractant is limited only by either (a) its solubility in the resin or mixture of resins used and/or (b) the volume ratio of microvoids in the polymer to said polymer and/or (c) the solubility of the insect attractant in the polymer on solidification. The proportion of insect attractant can in many instances go up to 45% by weight or even higher.

Thus, the proportion of insect attractant to resin can vary from small but effective amounts on the order of about 1% of the weight of the resin body up to about 45% by weight of the resin body. In general, it is preferred to use between about 5% up to about 30% based on the weight of resin body of the insect attractant. This is an optimum amount balancing the proportion of insect attractant against the time period over which the article emits the insect attractant and against the tendency of the insect attractant to "oil out". This "oiling out" is specifically avoided as a result of the use of foaming agent.

As stated, supra, various polymers are useful in the practice of our invention. Specific examples of polymers useful in the practice of our invention are as follows:

(a) DYLAN ® brand of low density polyethylene DYLAN ® is a trademark owned by the Atlantic Richfield Company of Los Angeles, Calif.;
(b) DYLITE ® of expandable polystryene compositions. DYLITE ® is a trademark of the Atlantic Richfield Company of Los Angeles, Calif.;
(c) SUPER DYLAN ® a high density polyethylene. SUPER DYLAN ® is a trademark of the Atlantic Richfield Company of Los Angeles, Calif.;
(d) Blended polyethylene and carbon black as specifically taught in U.S. Pat. No. 4,369,267 issued on Jan. 18, 1983, the specification for which is incorporated by reference herein;
(e) Polystyrene as disclosed in U.S. Pat. No. 4,369,227 issued on Jan. 18, 1983, the specification for which is incorporated herein;
(f) Polyene/alpha-olefin as exemplified and disclosed in U.S. Pat. No. 4,369,291, the specification for which is incorporation by reference herein;
(g) Poly-alpha-olefins as exemplified in Canadian Letters Patent No. 1,137,069 issued on Dec. 7, 1982, the specification for which is incorporated herein;
(h) Polymeric compositions as disclosed in Canadian Letters Patent No. 1,137,068 issued on Dec. 7, 1982, the specification for which is incorporated by reference herein;
(i) Poly-alpha-olefins disclosed in Canadian Letters Patent No. 1,137,067, the specification for which is incorporated by reference herein;
(j) Polyolefins described in Canadian Letters Patent No. 1,137,066, the specification for which is incorporated by reference herein;
(k) Polyethylene oxides as disclosed in Canadian Letters Patent No. 1,137,065 issued on Dec. 7, 1982, the specification for which is incorporated by reference herein;
(l) Olefin polymers and co-polymers as disclosed in Canadian Letters Patent No. 1,139,737, the disclosure of which is incorporated by reference herein. Canadian Patent No. 1,139,737 was issued on Jan. 18, 1983;
(m) Polyolefins disclosed in Canadian Letters Patent No. 1,139,738, the disclosure of which is incorporated by reference herein. Canadian Patent No. 1,139,738 was issued on Jan. 18, 1983;
(n) Chlorinated PVC as disclosed in *Polymer* 1982, 23 (7, Suppl.), 1051-6 abstracted at Chem. Abstracts 97:145570y, 1982;
(o) Polyepsilon caprolactone co-polymers made by means of alcohol initiated polymerization as disclosed in *J. Polym. Sci.* Polym. Chem. Ed. 1982, 20(2), pp. 319-326, abstracted at Chem. Abstracts. volume 96:123625x, 1982;

(p) Styrene acrylonitrile co-polymers as disclosed in Diss. Abstracts, Int. B, 1982, 42(8), 3346 and abstracted at Chem. Abstracts 96:143750n (1982);

(q) Co-polymers of epsilon caprolactone with 1,4-butane diol as disclosed at Kauch. Rezine,.1982, (2), 8–9, abstracted at Chem. Abstracts, Volume 96:182506g (1982);

(r) Polyesters as disclosed in U.S. Pat. No. 4,326,010, the specification for which is incorporated by reference herein;

(s) Chlorinated polyethylene as disclosed by Belorgey, et al, *J. Polym. Sci.* Polym. Phys. Ed. 1982, 20(2), 191–203;

(t) Plasticized polyepsilon caprolactone co-polymers containing dimethyl phthalate plasticizers as set forth in Japanese Patent No. J81/147844, abstracted at Chem. Abstracts, Volume 96:69984y (1982), the specification for which is incorporated by reference herein;

(u) Maleic anhydride modified adducts of polyepsilon caprolactone polyols and ethylenically unsaturated monomer as disclosed in U.S. Pat. No. 4,137,279 issued on Jan. 30, 1979, the specification for which is incorporated by reference herein;

(v) Polyurethane polymers having lactone backbones as disclosed in U.S. Pat. No. 4,156,067 issued on May 22, 1979, the disclosure of which is incorporated by reference herein;

(w) Polyurethane polyether resins wherein the resin is obtained by reacting a polyfunctional lactone with a long chain polyalkylene diol and a urethane precursor as disclosed in U.S. Pat. No. 4,355,550 issued on Mar. 10, 1981, the disclosure of which is, incorporated by reference herein; and (x) Resins having polyurethane backbones as disclosed in U.S. Pat. No. 3,975,350 issued on Aug. 17, 1976, the disclosure of which is incorporated by reference herein.

Optionally, downstream from the addition point of the insect attractant a gaseous or liquid containing blowing agent may be added (e.g., at barrel segments S-5, S-6, S-7, S-8 or S-9 and S-10) using the polymer addition barrel segment as a reference barrel segment "S-1". Examples of gaseous blowing agents are carbon dioxide, nitrogen, mixtures of nitrogen and carbon dioxide in proportions of from 1 up to 99% by volume nitrogen and 99 down to 1% by volume carbon dioxide, helium, mixtures of helium and nitrogen, mixtures of helium and carbon dioxide and other gases which are inert at the temperature and pressure of the polymer at the time of the extrusion operation Thus, gas containing oxygen or other reactive gases, e.g., hydrogen, should be avoided. The pressure of the gas blowing agent being added to the extruder at the point of addition may vary from about 80 up to about 150 psig. Higher pressures may be used without adversely affecting the usefulness of the foamed insect attractant-containing polymer particle.

The feed rate range of insect attractant may be between about 0.5% up to about 45% by weight of the polymer.

The die of the extruder may create rod, sheet, film or ribbon. The resulting product may then, if desired, be pelletized to form foamed insect attractant-containing polymer particles or the ribbon may be used "as-is" as an insect attractant-containing polymeric article of manufacture itself.

In addition to the optional gaseous blowing agents (which are necessarily "inert" gases), blowing agents may be added at some point on the extruder which will create gaseous voids in the insect attractant-containing polymeric articles of our invention and these "blowing agents" are well known to one having ordinary skill in the art. Examples of such non-gaseous containing materials which yield gases on admixture with the polymer in the extruder but which are still inert to the insect attractant are as follows:

(i) Under high pressure, ethylene, methane, propane, butane, propylene, methyl chloride, methyl bromide, vinyl chloride and methylene dichloride as more specifically described in U.S. Pat. No. 2,387,730, the specification for which is incorporated by reference herein;

(ii) Ordinarily liquid material such as n-pentane, isopentane, cyclopentane, hexane and petroleum ether fractions or halogen hydrocarbons such as $CFCl_3$, $CF_2Cl_2$, $CH_3Cl$, $CH_2Cl_2$ separately or in admixture with one another as set forth in U.S. Pat. No. 3,758,425, column 4, lines 1–5, the specification for which is incorporated by reference herein;

(iii) Dichlorotetrafluoroethane, tetramethylmethane, monochlorodifluoromethane, dichlorodifluoromethane, and dichlorotetrafluoroethane as specifically described in U.S. Pat. Nos. 2,948,664 and 2,948,665, issued on Aug. 9, 1960, the specifications for which are incorporated herein by reference; and (iv) Azo bis(formamide); diazoaminobenzene; N,N'-dinitrosopentamethylene tetramine; N,N'-dimethyl-N,N'-dinitrosoterephthalamide; p,p'-oxy-bis(benzene sulfonyl semicarbazide); azo bis(isobutyronitrile); p,p'-oxy-bis(benzene sulfonyl hydrazide); p,p'-diphenyl-bis(sulfonyl hydrazide); benzene-sulfonyl hydrazide; m-benzene-bis(sulfonyl hydrazide) as more specifically described in U.S. Pat. No. 3,298,975 issued on Jan. 17, 1967, the specification for which is incorporated by reference herein.

The resulting extruded (and if desired pelletized) material may then be, for example, injection molded to form a useful article. Such injection molding can be carried out in accordance with the procedure as set forth in U.S. Pat. No. 3,268,636 issued on Aug. 23, 1966, the specification for which is incorporated by reference herein.

DETAILED DESCRIPTION OF THE DRAWINGS

Referring to FIGS. 1, 2, 3 and 4, FIGS. 3 and 4 shown in detail the ZOECON ® sticky trap, more specifically a ZOECON PHEROCON ® 1C Trap (e.g., in FIG. 4 indicated by reference numeral (616a) and in FIG. 1 indicated by reference numerals 608c, 608d, 609a, 609b, 609c, 609d, 610a, 610c, 610d, 611a, 611c, 612a, 612c, 612d, 613a, 613c, 613d, 614a, 614b, 614c, 615a, 615c, 616a, 616b, 617a, 617b, 617c, 618a, 618b, 618c, 619c, 620a, 620b, 620c, 621a, 621b, 621c, 623a, 623b, 623c, 624a, 624b and 624c. The ZOECON PHEROCON ® 1C Trap has suspended in it as will be seen from FIGS. 3 and 4, a 2 cm×2 cm strip of slow release polymer (polyethylene) 6117 in FIGS. 3 and 4 containing insect attractant (benzyl formate, d-carvone, or d-pulegone or mixtures thereof containing from about 0.5% up to about 99% by weight of benzyl formate; from about 99% down to about 0.5% by weight of d-carvone; and from about 0.5% up to about 99% by weight of d-pulegone) or the 2 cm×2 cm strip contains the GOLDEN MALRIN® control. The 2 cm×2 cm strip 6117 is suspended in the trap 616a from bar 6116 using holder 6118. Trap 616a has lower tray 6110 which will catch insect droppings or dead insects which do not adhere to the 2 cm×2 cm strip 6117. The lower tray 6110 is attached via strips 6112a and 6112b to upper holder 6111 which is attached to suspension bar 6113 suspended by rod 6114 to the barn beam 6115 (in FIG. 2). The barn beam 6115 is held in a horizontal position by upright supports 602 and 606 (as will be seen in FIG. 2) which is firmly in place on the barn floor 6119. The 2 cm×2 cm strip 6117 is formulated in such apparatus as is set forth in FIG. 6 described in detail, infra. The traps containing the insect attractant, e.g, benzyl formate, d-carvone or d-pulegone or combinations thereof or the GOLDEN MALRIN® control are placed in the goat barn having fencing panels 601 and 603 and inner support 604 and 605, an observation post 622 and experimental locations 608, 609, 610, 611, 612, 613, 614, 615, 616, 617, 618, 619, 620, 621, 623 and 624 has suspended in it the several Zoecon Pherocon 1C Traps each containing 2 cm×2 cm strips of formulated slow release insect attractants. Trap placement was replicated in four quadrants of the barn. Traps 616a, 616b, 615a, 615c and other quadra traps were placed in the barn for seven days and the insects collected were identified and counted. Evidence of various insects visiting the traps were also counted, as fly specks inside or outside to the traps. All the test materials were compared with a standardized check treatment consisting of 0.5 grams of GOLDEN MALRIN® fly bait inside slow release packets hung like the other compounds as in strip 6117 in FIGS. 3 and 4.

Figure 5:
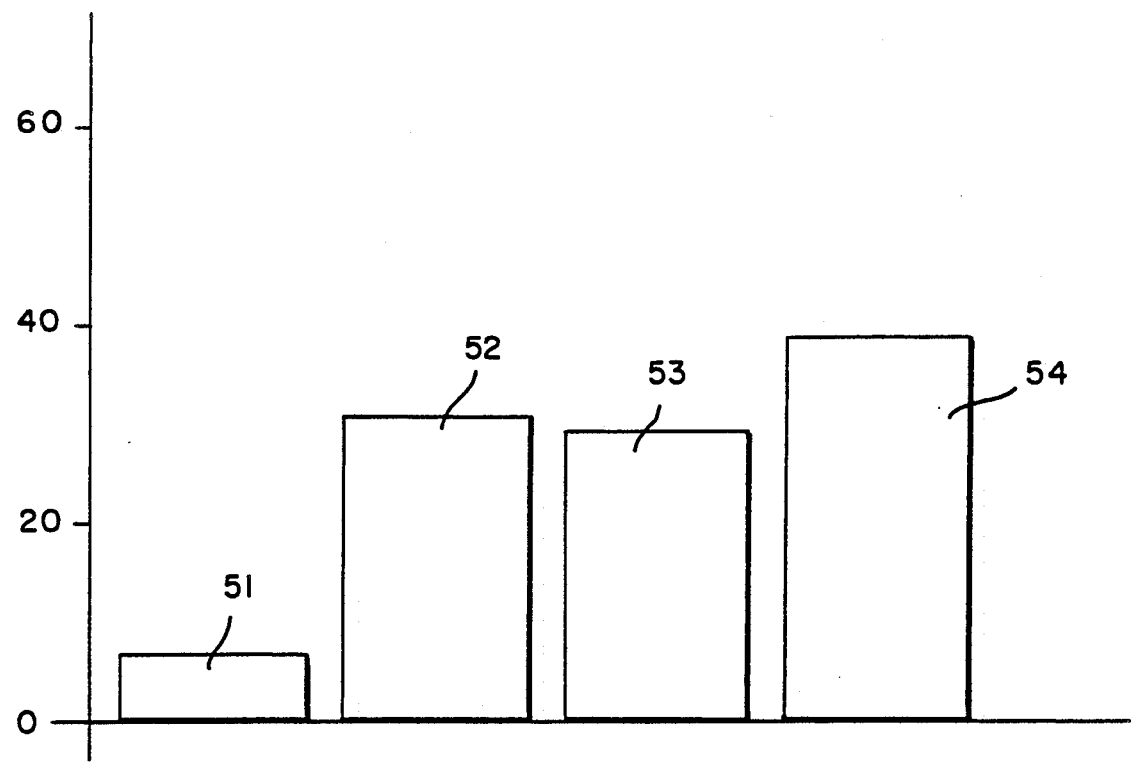
FIG. 5 is a bar graph showing a comparison of the field trial tests of attractants for house flies (*Musca domestica L.* (Diptera:Muscidae)) comparing benzyl formate, d-carvone, d-pulegone and GOLDEN MALRIN®, a mixture of (Z)-9-tricosene and methomyl which is methomyl(s-methyl N-[methylcarbamoyl]oxy)thioacetimidate the graph being compound vs. house fly specks per trap.

FIG. 5 indicates the results of field trial tests using the apparatus set forth in FIGS. 1, 2, 3 and 4.

FIG. 5 is a series of bar graphs for field trial tests of the attractants benzyl formate, d-carvone, d-pulegone and GOLDEN MALRIN® for house fly speck counts inside the traps indicated by reference numeral 6117. Thus, the bar graph indicated by reference numeral 52 is the bar graph for d-pulegone insofar as it attracts *Musca domestica L.* (Diptera:Muscidae) inside of such traps as trap 616a in FIGS. 3 and 4, the house fly specks being located on tray 6110 in FIGS. 3 and 4. Tray 6110 is also shown in FIG. 2. The bar graph indicated by reference numeral 53 is the bar graph for d-carvone insofar as it attracts *Musca domestica L.* (Diptera:Muscidae). The bar graph indiated b reference numeral 51 is the bar graph for GOLDEN MALRIN® (insofar as it attracts *Musca domestica L.* (Diptera:Muscidae). The bar graph indicated by reference numeral 54 is the bar graph for benzyl formate insofar as it attracts *Musca domestica L.* (Diptera:Muscidae). As stated, supra, FIG. 5 is a graph of fly specks/trap vs compound. Thus, the d-pulegone in FIG. 5 gives rise to an attractancy of *Musca domestica L.* (Diptera:Muscidae) of 30.0 fly specks/trap; the d-carvone gives rise to an attractancy of 28.8 fly specks/trap; and the benzyl formate gives rise to an attractancy of 38.4 fly specks per trap; and the GOLDEN MALRIN® gives rises to only 6.2 fly specks per trap.

Figure 6:
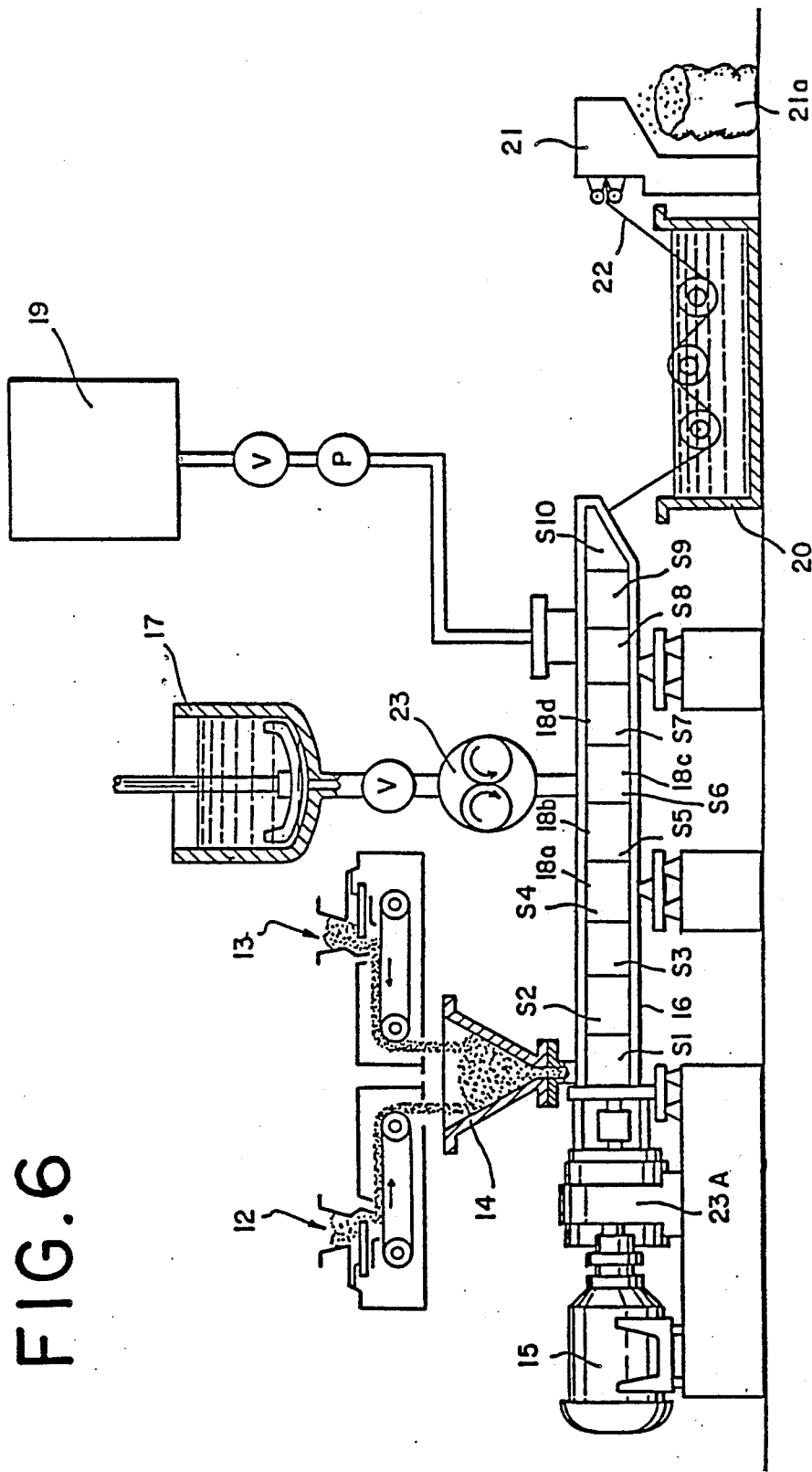
FIG. 6 is a cut-away side elevation schematic diagram of a screw extruder during the compounding of a resin with the insect attractants benzyl formate, d-carvone or d-pulegone or combinations thereof while simultaneously adding foaming agent into the hollow portion of the barrel of the extruder and incorporates the pelletizing apparatus used in pelletizing the extruded foamed tow product produced as a result of the extrusion operation.

FIG. 6 is a schematic cut-away elevation diagram of an extrusion and pelletizing apparatus useful in carrying out a process of our invention during the operation of said apparatus whereby the insect attractant is incorporated into a polymer such as a polyethylene. Motor 15 drives the extruder screws located at 23A in barrel 16, the extruder being operated at temperatures in the range of about 150° C. up to about 250° C. At the beginning of the barrel resin at source 12 together with additives, e.g., processing aids and densifiers at location 13 is added via addition funnel 14 into the extruder. Simultaneously (when the operation reaches "steady state"), insect attractant, benzyl formate, d-carvone, d-pulegone or mixtures of benzyl formate, d-carvone, benzyl formate and d-pulegone, d-carvone and d-pulegone or benzyl formate, d-carvone and d-pulegone is added to the extruder at one, two or more of barrel segments S-3, S-4, S-5, S-6, S-7 and S-8 of the extruder (which may be a twin screw or single screw extruder) at locations 18a, 18b, 18c and 18d (for example) by means of gear pump 23 from source 17. From source 19 into barrel segments S-5, S-6, S-7, S-8, S-9 and S-10, a gaseous or liquid blowing agent, e.g., nitrogen, carbon dioxide and the like as described, supra, are added simultaneously with the addition of the insect attractant, e.g., benzyl formate, d-carvone, or d-pulegone or combinations of benzyl formate, d-carvone and/or d-pulegone. The feed rate range of resin is about 80–300 pounds per hour. The feed rate range of the insect attractant is between 1 and 35% of the feed rate range of the resin. The blowing agent range is such that the pressure of the gas or the pressure over the liquid being fed into the extruder is between about 50 and 200 psig if, indeed, blowing agent is added. If desired, the extruded ribbon or cylinder may be passed through water bath 20 and pelletized in pelletizer 21 and then passed into collection apparatus 21a.

What is claimed is:

1. A method of attracting *Musca domestica L.* (Diptera:Muscidae) to an insect trap comprising the step of exposing the environment surrounding said trap to an insect attractant containing polymer which consists of a mixture of a polymer and from about 1% up to about 45% by weight of said polymer of a composition of matter selected from the group consisting of:
   (i) benzyl formate;
   (ii) d-carvone;
   (iii) d-pulegone;
   (iv) a mixture of benzyl formate and d-carvone;
   (v) a mixture of benzyl formate and d-pulegone;
   (vi) a mixture of d-carvone and d-pulegone; and
   (vii) a mixture of benzyl formate, d-carvone and d-pulegone.

said composition of matter being compatible with said polymer.

2. The method of claim 1 wherein the composition of matter is benzyl formate.

3. The method of claim 1 wherein the composition of matter is d-carvone.

4. The method of claim 1 wherein the composition of matter is d-pulegone.

5. The method of claim 1 wherein the composition of matter is a mixture of benzyl formate and d-carvone.

6. The method of claim 1 wherein the composition of matter is a mixture of benzyl formate and d-pulegone.

7. The method of claim 1 wherein the composition of matter is a mixture of d-carvone and d-pulegone.

8. The method of claim 1 wherein the composition of matter is a mixture of benzyl formate, d-carvone and d-pulegone.

* * * * *